(12) United States Patent
Schafer

(10) Patent No.: US 6,367,330 B1
(45) Date of Patent: Apr. 9, 2002

(54) DEFECT PARAMETER FOR WOODEN MEMBERS

(75) Inventor: Mark E. Schafer, Ambler, PA (US)

(73) Assignee: Perceptron, Inc., Plymouth Meeting, PA (US)

(*) Notice: Subject to any disclaimer, the term of this patent is extended or adjusted under 35 U.S.C. 154(b) by 0 days.

(21) Appl. No.: 09/641,168

(22) Filed: Aug. 17, 2000

Related U.S. Application Data

(60) Provisional application No. 60/203,304, filed on May 10, 2000, and provisional application No. 60/188,658, filed on Mar. 10, 2000.

(51) Int. Cl.⁷ .............................................. G01N 29/04
(52) U.S. Cl. ............................ 73/598; 73/597; 73/600; 73/602
(58) Field of Search .......................... 73/584, 598, 645, 73/579, 599, 600, 602, 646, 597

(56) References Cited

U.S. PATENT DOCUMENTS

| | | | |
|---|---|---|---|
| 5,024,091 A | * 6/1991 | Pellerin et al. | 73/597 |
| 5,095,465 A | * 3/1992 | Stokoe, II | 367/14 |
| 5,392,652 A | * 2/1995 | Levesque et al. | 73/629 |
| 5,396,799 A | * 3/1995 | Ross et al. | 73/579 |
| 5,760,308 A | 6/1998 | Beall et al. | 73/644 |
| 5,804,728 A | 9/1998 | Beall et al. | 73/598 |
| 5,824,908 A | * 10/1998 | Schindel et al. | 73/632 |
| 6,026,689 A | * 2/2000 | Snyder et al. | 73/602 |
| 6,029,522 A | * 2/2000 | Schafer et al. | 73/598 |
| 6,092,418 A | * 7/2000 | Schafer et al. | |

OTHER PUBLICATIONS

Beall, F.C., "Wood: Acoustic Emission and Acousto–Ultrasonic Characteristics", *Concise Encyclopedia of Materials Characteristics*; R.W. Cahn, Eric Lifshin, Eds., 1993, 551–554.

Beall, F.C., "Overview of Acoustic–Ultrasonic Applied to Wood and Wood–Based Materials", *Topical Conference Proceedings Book, 2ⁿᵈ Intern. Conf. On Acoustic–Ultrasonics*, Atlanta, GA, (Jun. 24–25), 1993, 153–161.

Kiernan, M.T., et al., "PC Analysis of an Acousto–Ultrasonic Signal", *Materials Evaluation*, 46, 1988, 1344–1352.

U.S. application No. 09/522,642, Schafer et al., filed Mar. 10, 2000.

* cited by examiner

*Primary Examiner*—Hezron Williams
*Assistant Examiner*—Jacques Saint-Surin
(74) *Attorney, Agent, or Firm*—Woodcock Washburn LLP

(57) ABSTRACT

The invention describes a method and system for detecting anomalies in a material. The method comprises the steps of transmitting waves through the object, receiving the waves after passage through the object, determining more than one reference characteristic, measuring more than one characteristic of the received wave, comparing a first reference characteristic with a first characteristic of the received wave to create a first factor, comparing a second reference characteristic with a second characteristic of the received wave to create a second factor, combining the first factor with the second factor to create a defect index, and identifying a location of one or more anomalies in the object using the defect index. The step of determining the reference characteristics may comprise transmitting another wave of known characteristics through a material free of anomalies to produce a standard wave, and measuring one or more characteristics of the standard wave. Alternatively, the step of determining the reference characteristics may comprise calculating the reference characteristics from known values of the transmitted wave. The method may further comprise the steps of moving the object such that another portion of the object may be interrogated by the waves. The reference characteristics may then be stored in a computer for further comparison with other received waves. Also, the method may further comprise outputting the locations of the identified anomalies to a grading apparatus for grading the object, or to a device that cuts the object.

30 Claims, 14 Drawing Sheets

DEFECT PARAMETER FOR WOODEN MEMBERS

RELATED APPLICATIONS

This application claims priority under 35 U.S.C. §119(e) to U.S. Provisional Patent Applications Serial No. 60/203,304, which was filed on May 10, 2000, and Ser. No. 60/188,658, which was filed on Mar. 10, 2000, and these applications are hereby incorporated by reference in their entireties.

TECHNICAL FIELD

The invention relates to the field of non-destructive testing. More specifically, the invention relates to the use of transmitted waves (e.g., ultrasonic) to make specific determinations regarding an object through which the wave passes.

BACKGROUND OF THE INVENTION

Non-destructive testing using ultrasonic waves is widely used in a number of testing environments, including the construction industry. For example, ultrasound testing techniques provide accurate grading of construction material, which in turn allows a builder to match the strength of the construction member to the type of construction project. In addition, proper grading permits manufacturers of the construction material, like sawmills for wooden members, to charge a premium for stronger members, while dedicating weaker members for more appropriate tasks.

In general, non-destructive testing systems operate by transmitting an ultrasonic wave of known characteristics through an object. The various anomalies of the material act upon the transmitted ultrasonic wave and modify its characteristics. The non-destructive testing system then collects the modified wave. By comparing the modified wave with its original form, or with a wave passing through a "standard" or "ideal" material, the non-destructive testing system is able to detect the various anomalies in the object. Moreover, the non-destructive testing system may be able to determine the type of anomaly, its location in the material, and its effect on the strength of the material.

To date, the process of comparing and analyzing the modified ultrasonic wave in order to detect anomalies has required the consideration of a number of the transmitted and collected characteristics or parameters of the waves. In fact, the necessary parameters usually vary depending on the material being tested. For example, because wooden members (e.g., trees, logs, cants, lumber, engineered and finished wood products) are highly non-homogeneous objects, causing severe distortion of the ultrasonic wave as it passes through, a greater number of parameters are necessary to determine the existence of, and to delineate the boundaries of defects in the wood (e.g., splits, knots, and grain distortions). These parameters may include a time-of-flight (or transmission time) of the ultrasonic wave through the wood member, energy, frequency, and other higher-order statistics statistical parameters. These higher order parameters can be used to describe the position (i.e., the centroid), shape (i.e., the skew) and distribution (i.e., kurtosis) of the waveform. A number of patents and publications discuss the parameters that may be used for defect recognition, as well as how specific conditions influence these parameters, including: Beall, F. C., et al., "*Wood: Acoustic Emission and Acousto-Ultrasonic Characteristics*" Concise Encyclopedia of Materials Characteristics, R. W. Cahn and Eric Lifshin, Eds. Pergammon Press, pp. 551–554, (1993); R. W. Cahn and Eric Lifshin, "*Concise Encyclopedia of Materials Characteristics*" eds. Pergammon Press, pp. 551–554, (1993); Beall, Frank C., "*Overview of Acousto-Ultrasonics Applied to Wood and Wood-Based Materials*", Topical Conference Proceedings Book, Second International Conference on Acousto-Ultrasonics, Atlanta, Georgia, Jun. 24–25, 1993, pp. 153–161; U.S. Pat. No. 5,760,308, entitled "Method and apparatus for non-destructively detecting hidden defects caused by bio-deterioration in living trees and round wood materials"; and U.S. Pat. No. 5,804,728 "Method and apparatus for non-intrusively detecting hidden defects caused by bio-deterioration in living trees and round wood materials." In addition, Kiernan, M. T., et al., "*PC Analysis of an Acousto-Ultrasonic Signal*", Materials Evaluation, 46, pp. 1344–1352, September 1988, provides a comprehensive description of acousto-ultrasonic parameters. Also, in U.S. Pat. No. 6,029,522 to Schafer and Ross, entitled "*Ultrasonic Apparatus for Characterizing Wooden Members,*" in which the present inventor is a co-inventor, two parameters, insertion Loss and pulse length, are collected and an independent anomaly detection analysis is conducted on each.

These current approaches, however, are restricted in their limited scope either by focusing on a single anomaly with limited parameters, or by requiring the concurrent examination of multiple parameters to determine the existence of, or delineate the boundaries of the anomalies in the object. In particular, the current techniques have failed to provide a single and robust parameter that provides anomaly detection capability, flexibility in the type of anomaly detected, relative immunity to non-anomaly signal changes (i.e., noise), and flexibility in additional signal processing approaches that permit the detection device to be "tuned" to certain anomalies.

Therefore, it would be advantageous to provide a system for detecting anomalies in an object that uses a single flexible parameter. The parameter should not only reliably indicate anomalies, but also it should be relatively immune to other changes in signal conditions caused, for example, by variations in contact pressure, or other insignificant variations in the object itself. That is, the parameter should show some specificity for defects and immunity from "noise."

SUMMARY OF THE INVENTION

The invention describes a method and system for detecting anomalies in a material. The method comprises the steps of transmitting waves through the object, receiving the waves after passage through the object, determining more than one reference characteristic, measuring more than one characteristic of the received wave, comparing a first reference characteristic with a first characteristic of the received wave to create a first factor, comparing a second reference characteristic with a second characteristic of the received wave to create a second factor, combining the first factor with the second factor to create a defect index, and identifying a location of one or more anomalies in the object using the defect index. The step of determining the reference characteristics may comprise transmitting another wave of known characteristics through a material free of anomalies to produce a standard wave, and measuring one or more characteristics of the standard wave. Alternatively, the step of determining the reference characteristics may comprise calculating the reference characteristics from known values of the transmitted wave. The method may further comprise the steps of moving the object such that another portion of the object may be interrogated by the waves. The reference characteristics may then be stored in a computer for further comparison with other received waves. Also, the method may further comprise outputting the locations of the identified anomalies to a grading apparatus for grading the object, or to a device that cuts the object.

The system for detecting anomalies in an object in accordance with the invention comprises a waveform generator that creates waves with one or more characteristics, a transmitting transducer in communication with the ultrasonic waveform generator that transmits the waves through the object, a receiving transducer that receives the waves after passage through the object, and a computer in communication with the receiving transducer and the transmitting transducer. The computer stores reference characteristics and compares a first reference characteristic with a first characteristic of the received wave to create a first factor. The computer also compares a second reference characteristic of with a second characteristic of the received wave to create a second factor. The computer then combines the first factor with the second factor to create a defect index. The computer then identifies a location of one or more anomalies in the object using the defect index. The system may further comprise a display device in communication with the computer, such that the display device displays a graphical map of one or more anomalies within the object. The system may further comprise a conveyor device that moves the object between the transmitting transducer and the receiving transducer. A positional encoder may be in communication with the conveyor device and the computer, such that the positional encoder provide the computer with a position of the object with respect to the transmitting transducer and the receiving transducer. In one embodiment, the object may comprise wood and be interrogated by ultrasonic waves.

Further benefits and advantages of the present invention will become more apparent in the detailed description provided below.

DETAILED DESCRIPTION OF THE PREFERRED EMBODIMENT

System Overview

Although the following description describes the invention in the context of wooden members, it should be appreciated that the invention may apply to other objects, as well. In addition, although portions of the following description depict the use of ultrasonic waves, it should be appreciated that the invention may employ waves of other types (e.g., electromagnetic) or acoustic waves within other frequency ranges (e.g., seismic and sonar).

Figure 1:
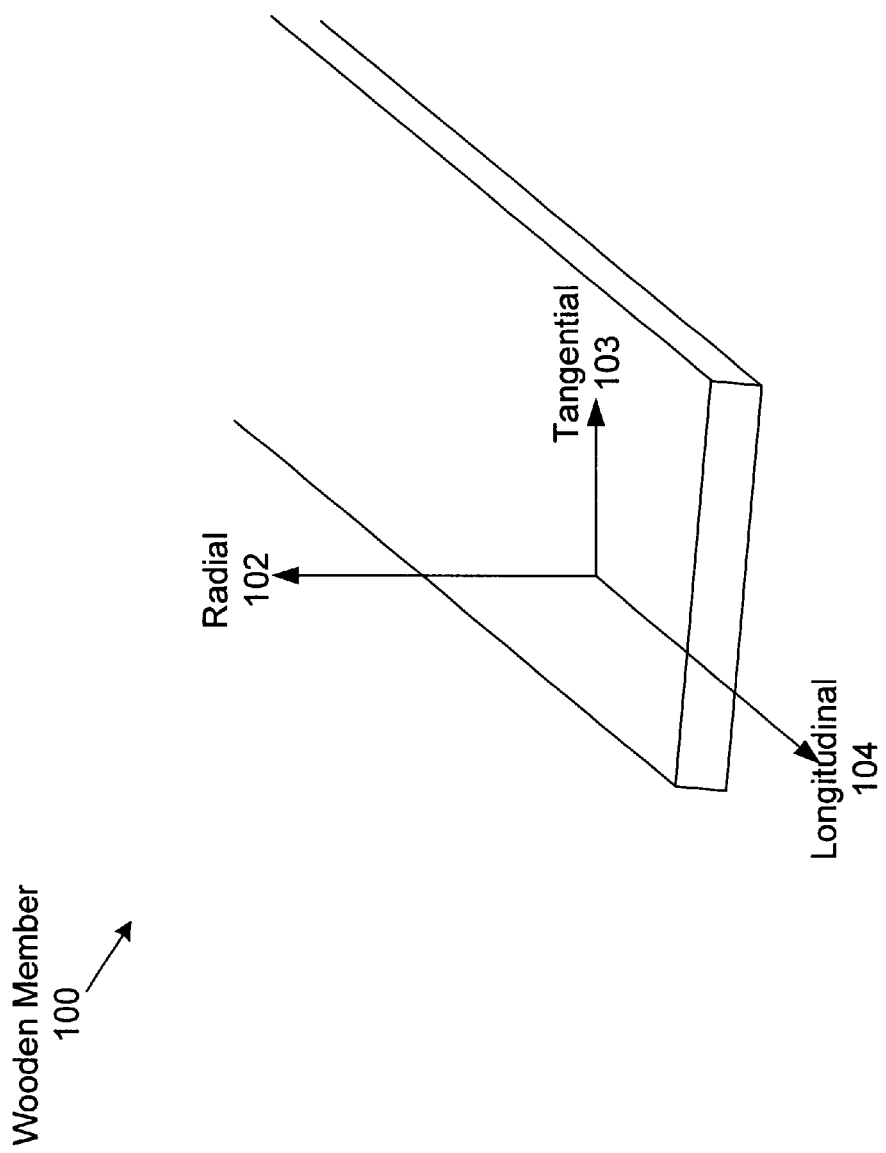
FIG. 1 is a depiction of a wooden member, showing the orientation of the grain direction in the wood.

FIG. 1 provides a standard orientation for a wooden member 100 for the invention, so as to facilitate the following discussion. A longitudinal direction 101 is along the fiber orientation, that is, in the direction of the trunk of the tree. A radial direction 102 is across all the rings and therefore across the grain of wooden member 100. A tangential direction 103 travels with the ring of the tree. It is well known in the art that the speed of sound in wooden member 100 is affected by the grain orientation. As a result, the speed of sound is about 5000 meters per second (m/s) in longitudinal direction 101, about 1200 m/s in radial direction 102, and about 1500 m/s in tangential direction 103. Significantly, because many defects (e.g., knots) involve significant changes in grain orientation, there will be a severe effect on ultrasonic wave propagation through regions with these defects. Although FIG. 1 shows wooden member 100 in the shape of a board, it should be appreciated that wooden member 100 may include standing timber, logs, cants, and engineered wood products. It should also be appreciated that the invention is not limited to interrogating wooden members, but may be used to interrogate other substances as well.

Figure 2:
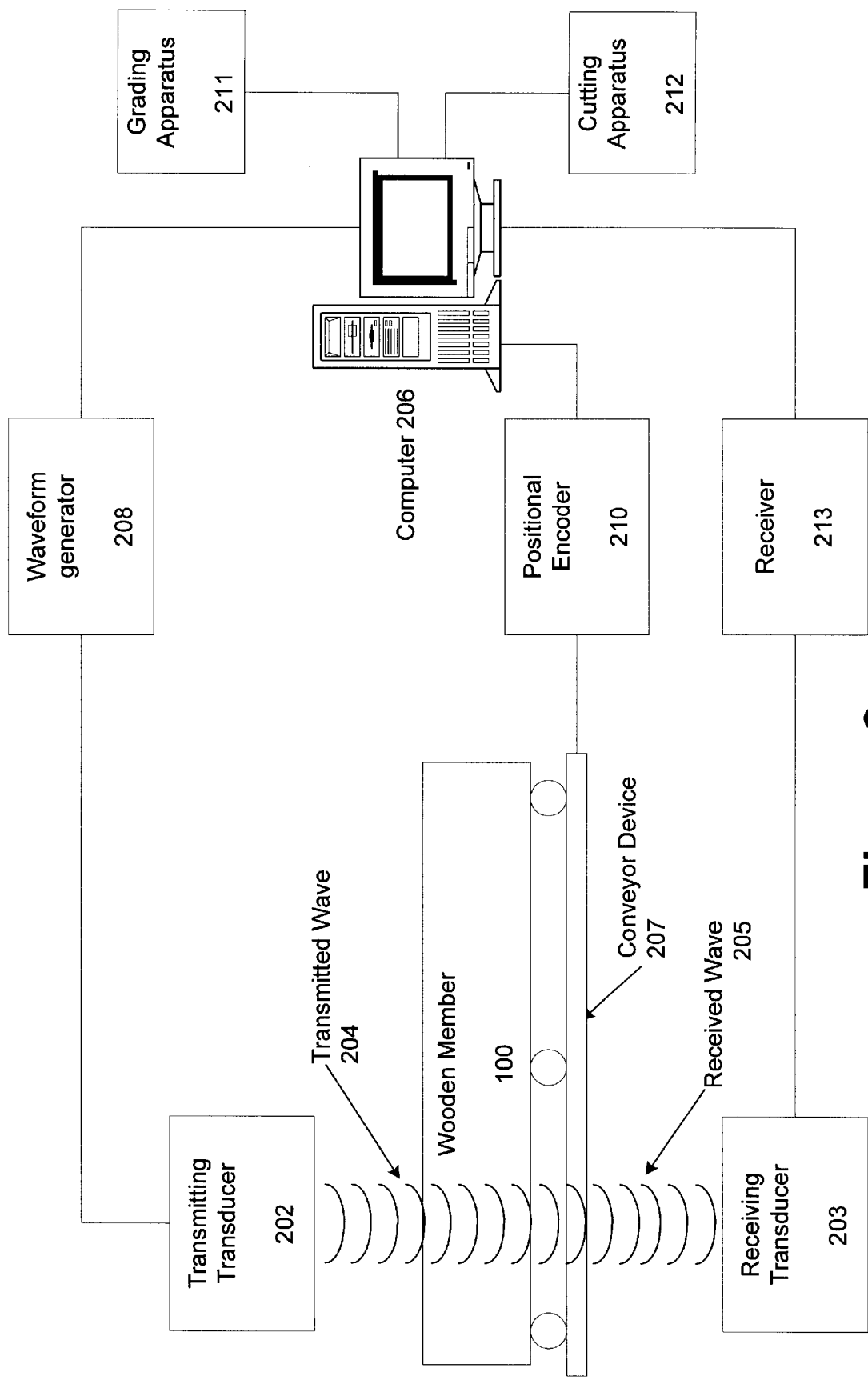
FIG. 2 is a block diagram of an anomaly detection system in which the invention may be implemented.

FIG. 2 is a block diagram of an anomaly detection system in which the invention may be implemented. As shown in FIG. 2, a waveform generator 208 is coupled to a transmitting transducer 202. Transmitting transducer 202 is located on one side of wooden member 100, and a receiving transducer 203 is located on the other side of wooden member 100. A conveyor device 207 moves wooden member 100 between transmitting transducer 202 and receiving transducer 203 so that the entire member may be interrogated for anomalies. Conveyor device 207 is coupled to a computer 206 via a positional encoder 210. Positional encoder 210 provides information regarding the position of wooden member 100 with respect to transmitting transducer 202 and receiving transducer 203. Computer 206 is further coupled to waveform generator 208 and receiver 213. Computer 206 also may be coupled to a grading apparatus 211 and a cutting apparatus 212. Grading apparatus 211 may be any device that is capable of labeling wooden member 100, based on its detected anomalies. Such labeling may be physical (e.g., a spray marking at a specific location to denote a defect or a color spray to denote overall grade) or electronic (e.g., information is stored in a computer-readable medium in a way that corresponds to the given wooden member). Cutting apparatus 212 may be a saw, for example, that cuts wooden member 100 depending upon the detected anomalies detected by the system.

In operation, waveform generator 208 provides electrical energy to transmitting transducer 202 . Transmitting transducer 202 then converts the electrical energy to another form of energy, for example, ultrasonic energy. Transmitting transducer 202 then sends a transmitted wave 204 through wooden member 100 and onto receiving transducer 203 . A received wave 205 represents transmitted wave 204 after it passes through wooden member 100. As will be described, received wave 205 has different characteristics from transmitted wave 204 such that comparison of the waves permits identification and mapping of anomalies in wooden member 100. Receiving transducer 203 then passes received wave 205 onto receiver 213. Receiver 213 converts the analog-based received wave 205 to a digital signal capable of being inputted to computer 206. In addition, receiver 213 may have amplifier capabilities (e.g., a gain stage) necessary to allow computer 206 to further process and investigate the wave.

Computer 206 is in communication with waveform generator 208 and receiver 213. As will be described, computer 206 processes signals received from receiver 213 and waveform generator 208 so as to identify the presence and location of anomalies within wooden member 100. Computer 206 also receives positional information regarding wooden member 101 via positional encoder 210. Therefore, computer 206 may compare transmitted wave 204 with received wave 205 and provide a graphical map of the defects within wooden member 100. Computer 206 is further coupled to waveform generator 208. Computer 206 may communicate information directly with waveform generator 208 so as to cause waveform generator to create a specific fire s pattern. Waveform generator, in turn can send back a digital representation of the transmitted voltage sent to transmitting transducer 202 . Such information indicates the characteristics of the provided electrical energy, and thus may be compared with the characteristics of received wave 205 to detect anomalies. For example, computer 206 may store information regarding the original parameters of the electrical energy provided by waveform generator 206, and then continuously compare each of the waves as they are sent to computer 206 from receiving transducer 203 . In addition, coupling computer 206 with waveform generator 208 allows computer 206 to vary the parameters of the electrical energy provided by waveform generator 208. For example, computer 206 may be used to vary the frequency, the voltage, and the number of pulses for the electrical energy provided by waveform generator 208.

It should be appreciated that the depiction of transmitting transducer 202 and receiving transducer 203 is schematic only. In practice, there may be a plurality of transmitter and receiver devices embodied in other forms, including a rolling element on conveyor device 207 as described in U.S. Ser. No. 09/522,642 U.S. patent application Ser. No. 60/177, 830, "Roller Mechanism Using an Array of Ultrasound Elements to Interrogate Wood Properties," which was filed on Mar. 10, 2000.

Anomaly Detection Method

Figure 3:
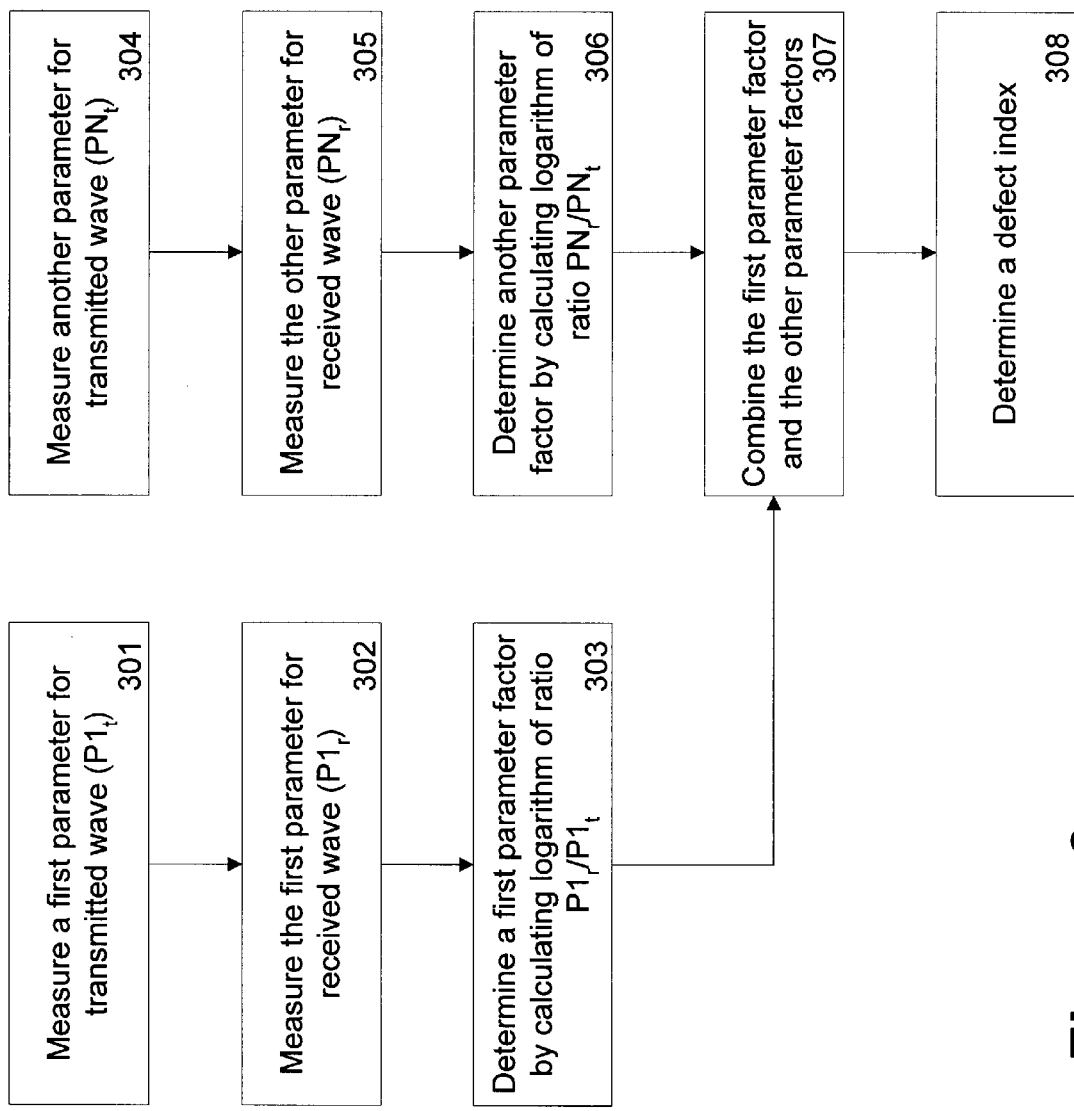
FIG. 3 is a flow diagram of a method for detecting anomalies in an object, according to the invention.

FIG. 3 is a flow diagram of a method for detecting anomalies in an object, according to the invention. In step 301, a first parameter (P1) is measured for transmitted wave 204 and designated as $P1_t$. In step 302, the first parameter (P1) is measured for received wave 205 and designated as $P1_r$. In step 303, a first parameter factor is determined by calculating a logarithm of the ratio of $P1_r/P1_t$. This calculation may be accomplished by computer 206. In step 304, another parameter (PN) is measured for transmitted wave 204 and designated $PN_t$, where N represents the $n^{th}$ parameter that is measured. Therefore, as will be discussed, any number of parameters (i.e., 1 . . . n) may be measured and used in calculating a defect parameter in accordance with the invention. In step 305, the other parameter (PN) is measured for received wave 205 and designated $PN_r$. In step 306, another parameter factor is determined by calculating a logarithm of the ratio of $PN_r/PN_t$. The other parameter factor also may be determined by computer 206.

In step 307, the first parameter factor and the other parameter factor(s) are combined. It should be appreciated that in step 307 any number of parameter factors (i.e., n factors) may be combined. It should also be appreciated that the combination of parameter factors may in step 307 may include any mathematical combination designed to maximize the detection of anomalies in wooden member 100. Such combination of parameter factors may be conducted by computer 206. As a result of the combination in step 307, a defect index is determined in step 308. Significantly, taking the logarithm of these parameter ratios permits their combination and results in a single defect index parameter in step 308. Specifically, parameters that are of widely disparate physical or mathematical units, such as energy, time, waveform skew, etc., may be combined. Therefore, the defect index may be represented by the following general formula:

$$\text{Defect Index (dB)} = IL \pm 20\log\left[\frac{P1_r}{P1_n}\right] \pm 20\log\left[\frac{P2_r}{P2_n}\right] \ldots \pm 20\log\left[\frac{Pn_r}{Pn_n}\right]$$

As will be discussed with reference to the various embodiments, the parameter that is selected to be measured in steps 301–302 and 304–305 may be any of the relevant characteristics of transmitted wave 204 and received wave 205, respectively. In fact, the invention allows the relevant characteristics to be varied. Moreover, the number (N) of parameter factors that are used, and how those factors are combined also may be varied. These variations may depend on one or more of the following circumstances: the nature of the object in question, the expected characteristics of the defects, the orientation and frequency of the ultrasonic waves, the ambient conditions in which the parameters are measured (e.g., a saw mill) etc. As a result, the defect index may be "tuned" to the specific environment in which anomaly detection is conducted. Finally, it should be appreciated that the relevant parameters may be measured from transmitted wave 204 and received wave 205 through a number of methods, well known by those skilled in the art, and discussed as relevant to the invention. With regard to the measured parameters for transmitted wave 204, it should be appreciated that "nominal" values may be calculated for transmitted wave 204 for those parameters that cannot be referred back directly to the transmit conditions on transmitting transducer 202 . Some of these methods will be discussed as they pertain to the disclosed embodiments. It should be appreciated, however, that the disclosed methods are not exclusive.

Defect Index using Insertion Loss and Pulse Length

Figure 4:
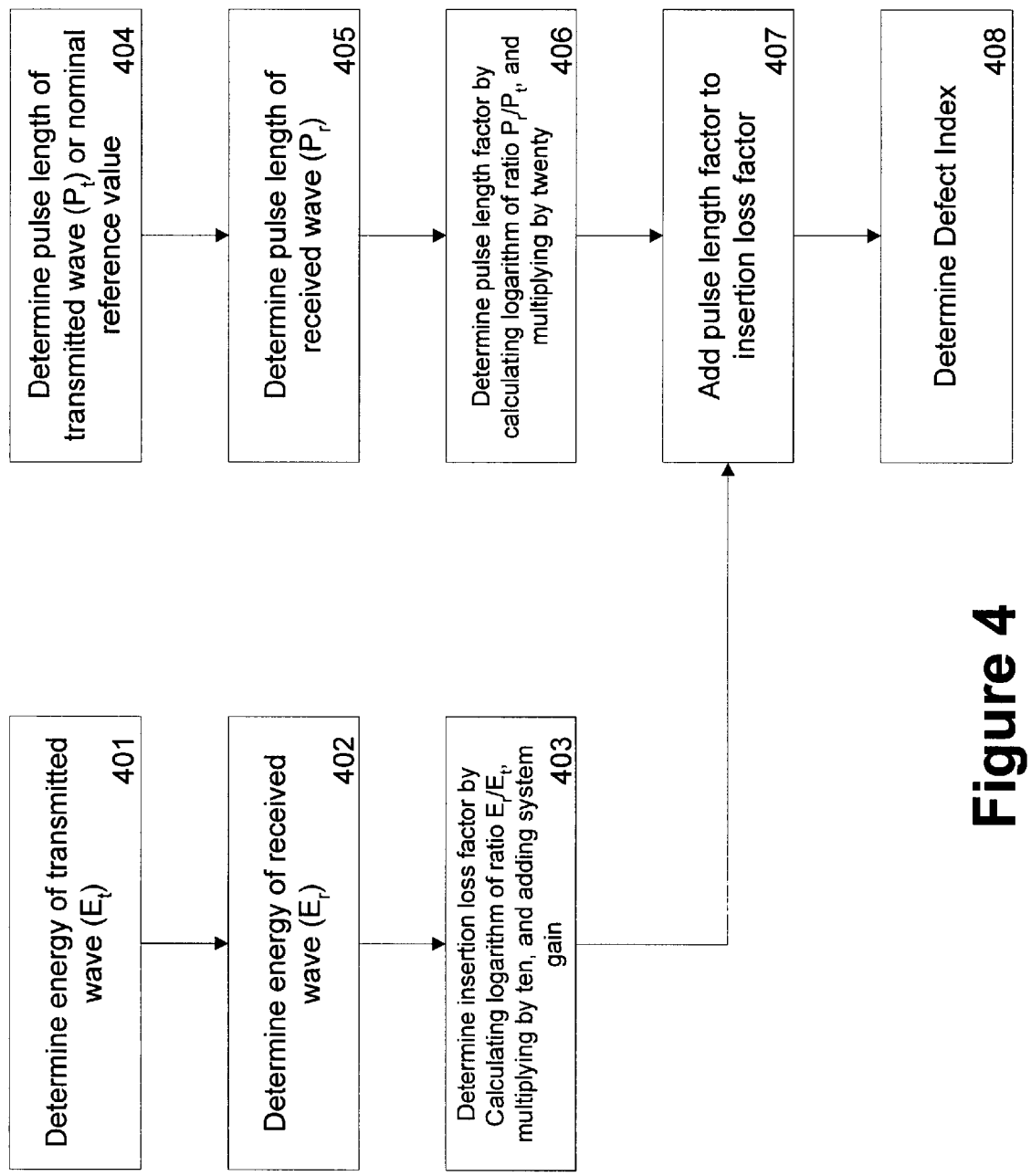
FIG. 4 is a flow diagram detailing one example for identifying defects in an object, according to the invention.

FIG. 4 is a flow diagram detailing one example for identifying defects in an object, according to the invention. In particular, FIG. 4 demonstrates the use of pulse length and energy parameters to determine the defect index. In step 401, the transmitted energy ($E_t$) is determined. Transmitted energy may be determined using any number of methods, well known to those skilled in the art. For example, transmitted energy may be calculated using values set on transmitting transducer 202 or by analyzing transmitted wave 204. In particular, transmitted energy may be determined by considering transmitted voltage (V), frequency (f), and number of cycles in the transmit waveform (N) of transmitting transducer 202. Then, the transmitted energy ($E_t$) can be calculated using the following formula:

$$E_t = NV^2/f$$

Under the assumption of a standard load of 1 ohm, this may be considered to be an equivalent power in Watt-seconds, or Joules. In step 402, the received energy ($E_r$) is determined. Received energy also may be determined using any number of methods, well known to those skilled in the art. For example, the received energy may be determined by analyzing received wave 205 using computer 206. In particular, wave energy is defined as the time integral of the voltage squared, or:

$$E = \int v^2(t)dt \text{ (in units of } V^2\text{-seconds)}$$

Again, under the assumption of a standard load of 1 ohm, this may be considered to be an equivalent power in Watt-seconds, or Joules. Also, as with other parameters, the calculated received energy value may be normalized by considering external influences, like system loss or receiver gain. For example, transmitted wave 204 may be sent from transmitting transducer 202 to receiving transducer 203 without passing through any object (i.e., with the transmitting and receiving transducers in direct contact). By comparing the transmitted energy to the received energy with transmitting transducer 202 in direct contact with receiving transducer 203, energy lost in the system between transmitting transducer 202 and receiving transducer 203 (e.g., ambient losses) may be determined. This similarly may be accomplished for other transmitter/receiver pairs (not shown). The system loss then may be used to adjust the received energy value to more accurately represent the energy lost as a result of passing through the object. It should be appreciated that the transmitted and received energies may be calculated by computer 206 as a function of the signals received from the various components in the system (as shown in FIG. 2).

Once the transmitted and received energies have been determined, an insertion loss (IL) factor may be determined in step 403. Insertion loss commonly is defined as the ratio of the received energy ($E_r$) to the transmitted energy ($E_t$). Taking into account any gain (G) of receiving transducer 203, the insertion loss factor may be calculated as follows:

$$IL(\text{db}) = 10\log\left[\frac{E_r}{E_t}\right] - G$$

Computer 206 may be programmed to perform this mathematical calculation. Notably, the insertion loss factor normally is expressed in decibels, and is a negative number because the system cannot receive more energy than was input into the system under the basic principle of conservation of energy.

In step 404, a transmitted pulse length ($P_t$) is determined. As with the other parameters, the transmitted pulse length may be determined using any number of methods, well known to those skilled in the art. For example, the pulse length may be estimated directly from the characteristics of transmitting transducer 202 and transmitted wave 204. In particular, using the number of cycles (N) and the frequency (f) of transmitted wave 204, where T=1/f is the time of a single cycle waveform, the transmitted pulse length may be calculated by computer 206, using the following formula:

$$PL_t = N\tau = N/f$$

In step 405, a received pulse length ($P_r$) is determined for received wave 205. The received pulse length may be determined using a number of methods, including the wave energy formula, described above. Specifically, pulse length commonly is defined as 1.25 times the duration time required for the wave energy to rise from 10% to 90% of its final energy. Thus, using the wave energy formula described above, the integral is determined at the specific times at which the wave energy crosses the ten percent and ninety percent thresholds, as follows:

$$e(t) = \int_0^t v^2(t)dt, \text{ where } e(t) \text{ is the voltage integral at time t.}$$

The total energy is then $E = e(t_{final})$. So, it follows that the time to the 10% and 90% energy points can be defined as the times that satisfy the equations:

$$e(t_{10\%}) = 0.1E \quad e(t_{90\%}) = 0.9E$$

And, therefore, the received pulse length is:

$$PL_r = 1.25 * (t_{90\%} - t_{10\%})$$

Computer 206 may be programmed to perform these mathematical calculations. Notably, the transmitted pulse length similarly may be determined, where for example, the transmit characteristics are not known and cannot be determined.

Once the transmitted and received pulse lengths are determined, a pulse length factor may be calculated. In step 406, the pulse length factor is calculated as the logarithm of the ratio of the received pulse length to the transmitted pulse length ($PL_r/PL_t$), multiplied by a factor of 20. In step 407, the pulse length factor determined in step 406 and the insertion loss factor, determined in step 403 are combined by adding the two. Notably, taking the logarithm of these energy and pulse length ratios permits their summation, and results in a single defect index parameter in step 408. Therefore, in one embodiment where insertion loss and pulse length are used as the parameters, the Defect Index (DI) may be determined by computer 206, using the following equation:

$$DI(\text{dB}) = IL - 20\log\left[\frac{PL_r}{PL_t}\right]$$

Figure 5:
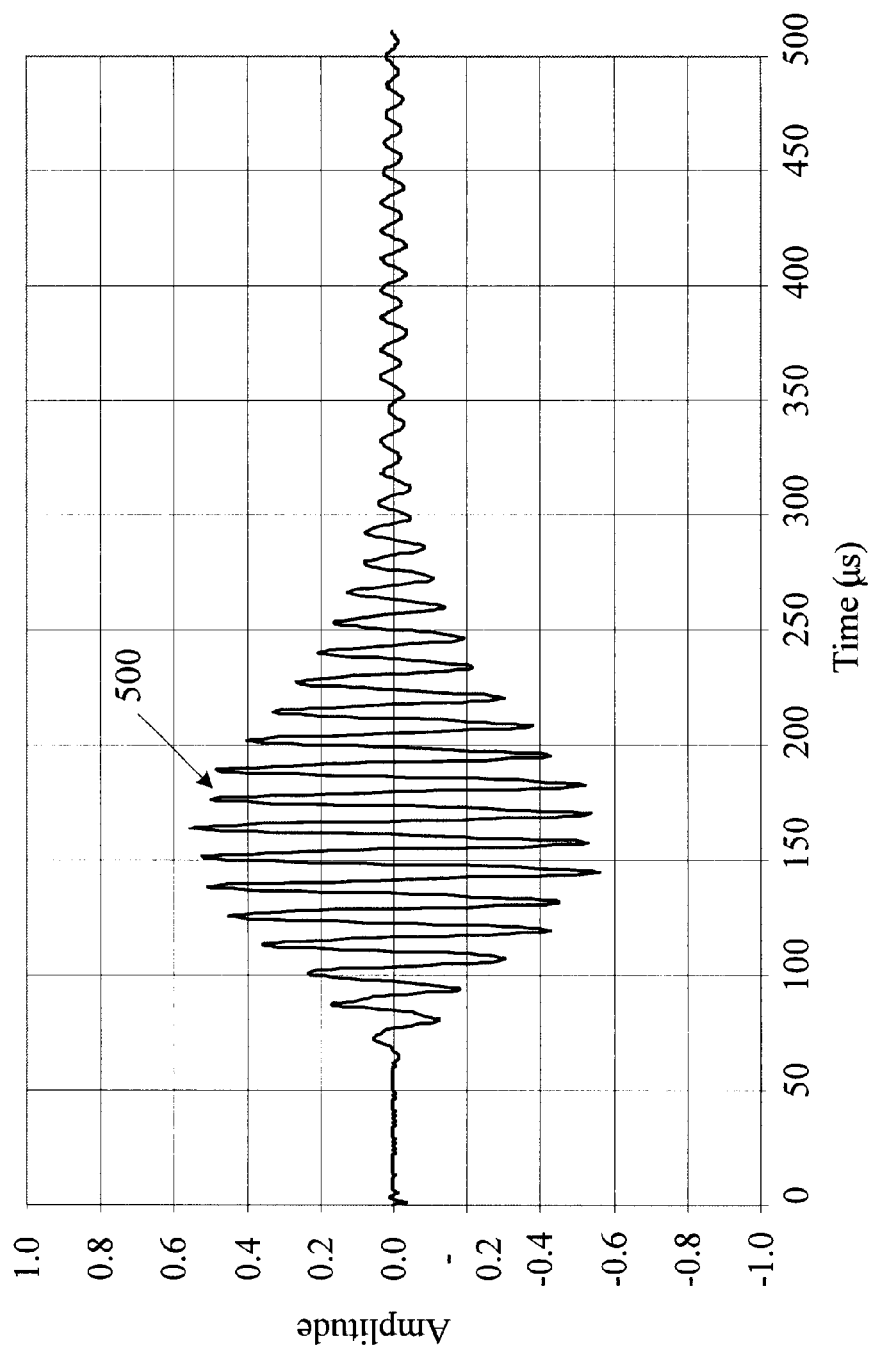
FIG. 5 is a graph of the voltage-signal strength over time for a "standard" ultrasonic wave passed through a defect free wooden member, measured using techniques known in the art.
Figure 6:
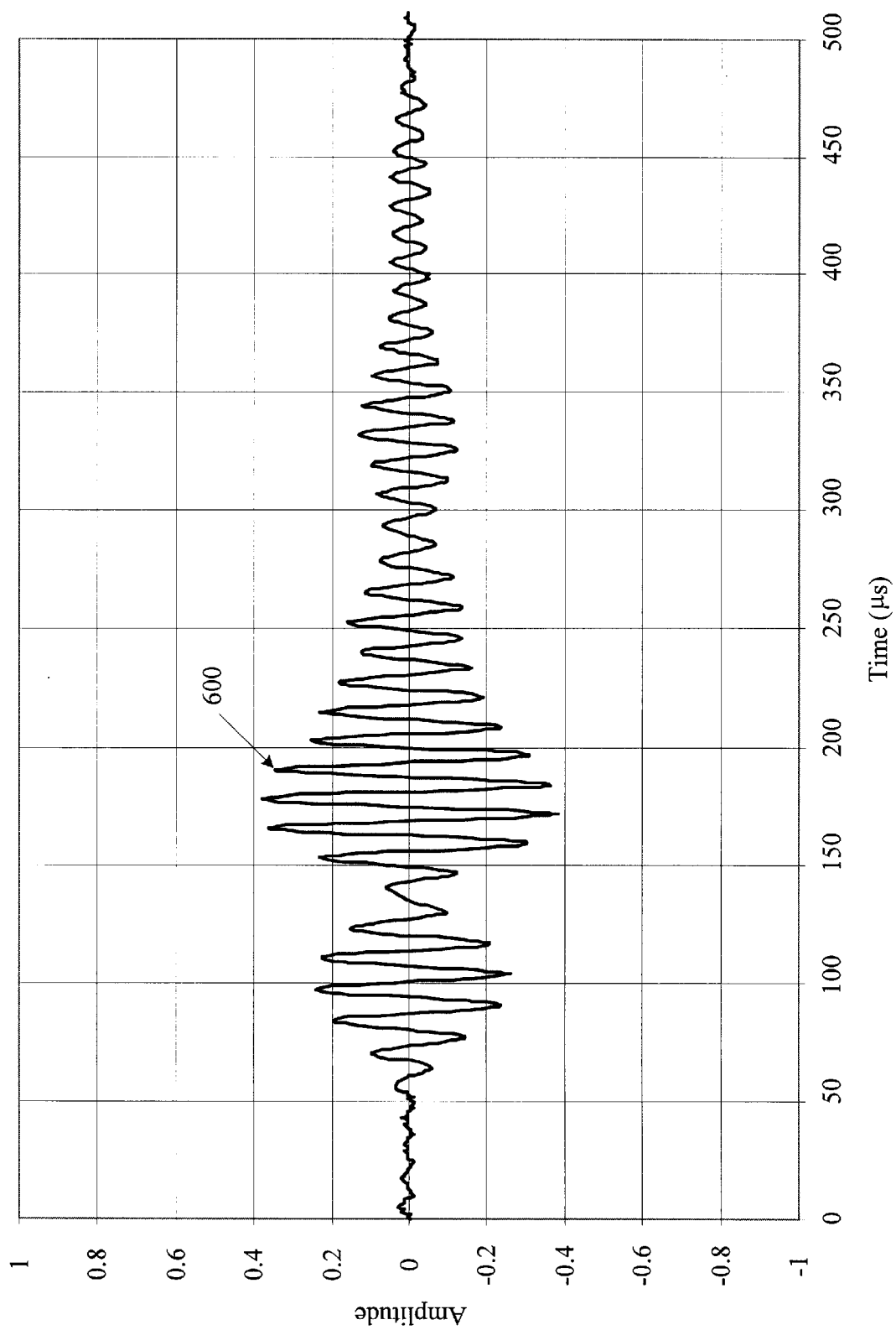
FIG. 6 is a graph of the voltage-signal strength over time for an ultrasonic wave passed through a wooden member containing a defect, measured using techniques known in the art.

FIGS. 5 and 6 provide graphical representations of received wave 205 under different conditions. FIG. 5 is a graph of voltage-signal strength over time for a waveform 500 that has passed through a normal, non-defective wooden object. Notably, the overall shape of waveform 500 is relatively compact and the amplitude distribution is Gaussian in nature. FIG. 6 is a graph of voltage-signal strength over time for a waveform 600 that has passed through a defective area of the wooden object. Notably, the amplitude of waveform 600 is less than the amplitude of waveform 500. Additionally, the energy of waveform 600 is dispersed over a longer time interval than waveform 500. These changes demonstrate the unique feature of defects in non-homogeneous materials, like wooden objects, where the changes reflect anomalies that generally are associated with additional acoustic paths through the object caused by changes in grain orientation. The invention's method for identifying the defect parameter determined in step 308 (as shown in FIG. 3), exploits this feature of defects in non-homogeneous materials. Specifically, the change demonstrated between waveform 500 and waveform 600 represents a combination of two effects in the wooden member: decreased signal level because of additional attenuation along the signal path, and extended pulse duration, because of additional signal paths through grain distortion and knots. Thus this implementation (as discussed with reference to FIG. 3) of this method has captured both phenomena.

Using pulse length and insertion loss alone to determine the defect index may be more suitable in some circumstances than in others. For example, where transmitted wave 204 is transmitted across the grain of a wooden member (e.g., across the face of a plank), knot defects may be expected to be substantially perpendicular to the direction of transmitted wave 204, and thus may be more readily detected by the defect index. This is illustrated in FIGS. 7 and 8.

Figure 7:
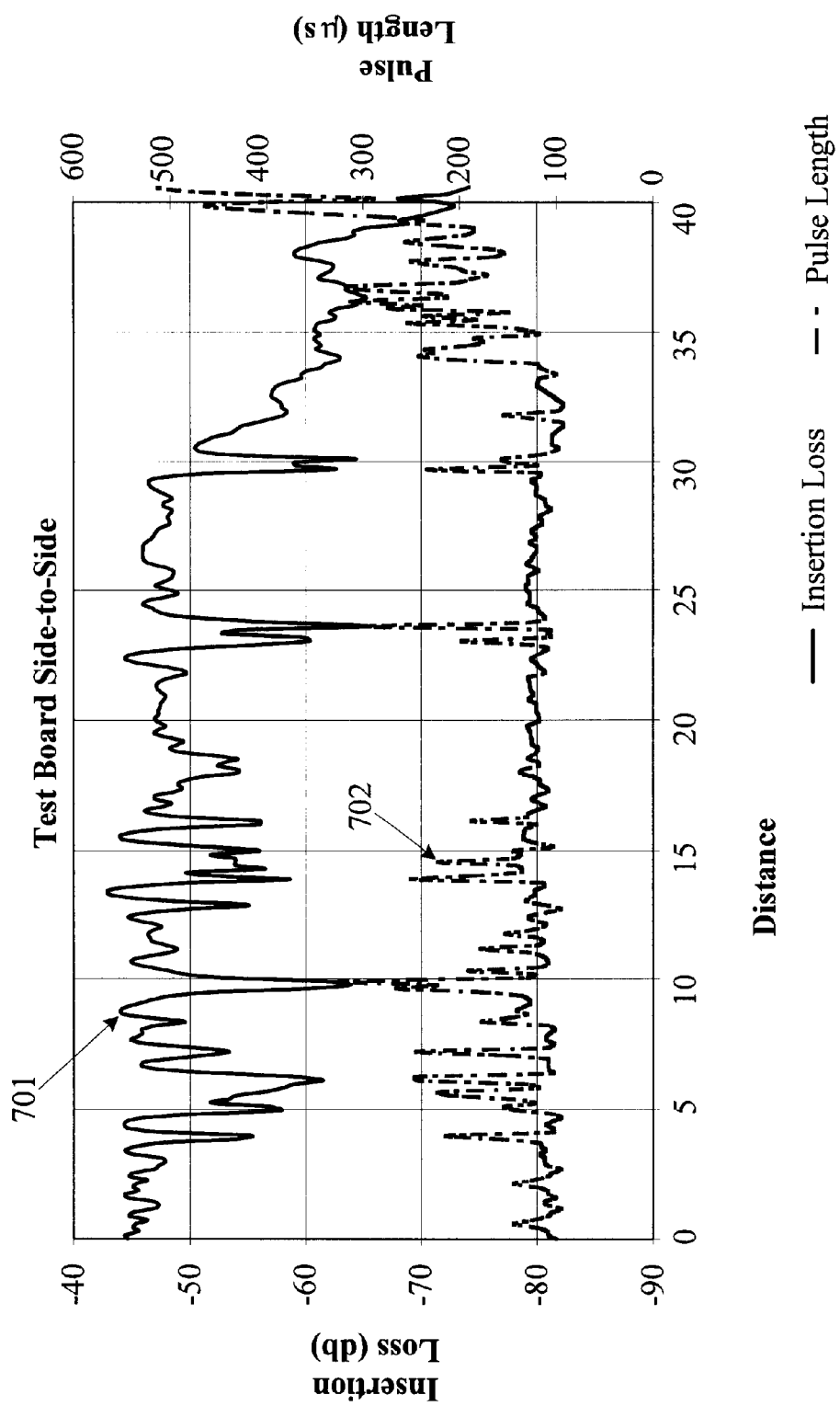
FIG. 7 is a graph of the insertion loss and the pulse length as a function of position along a wooden member, according to the invention.
Figure 8:
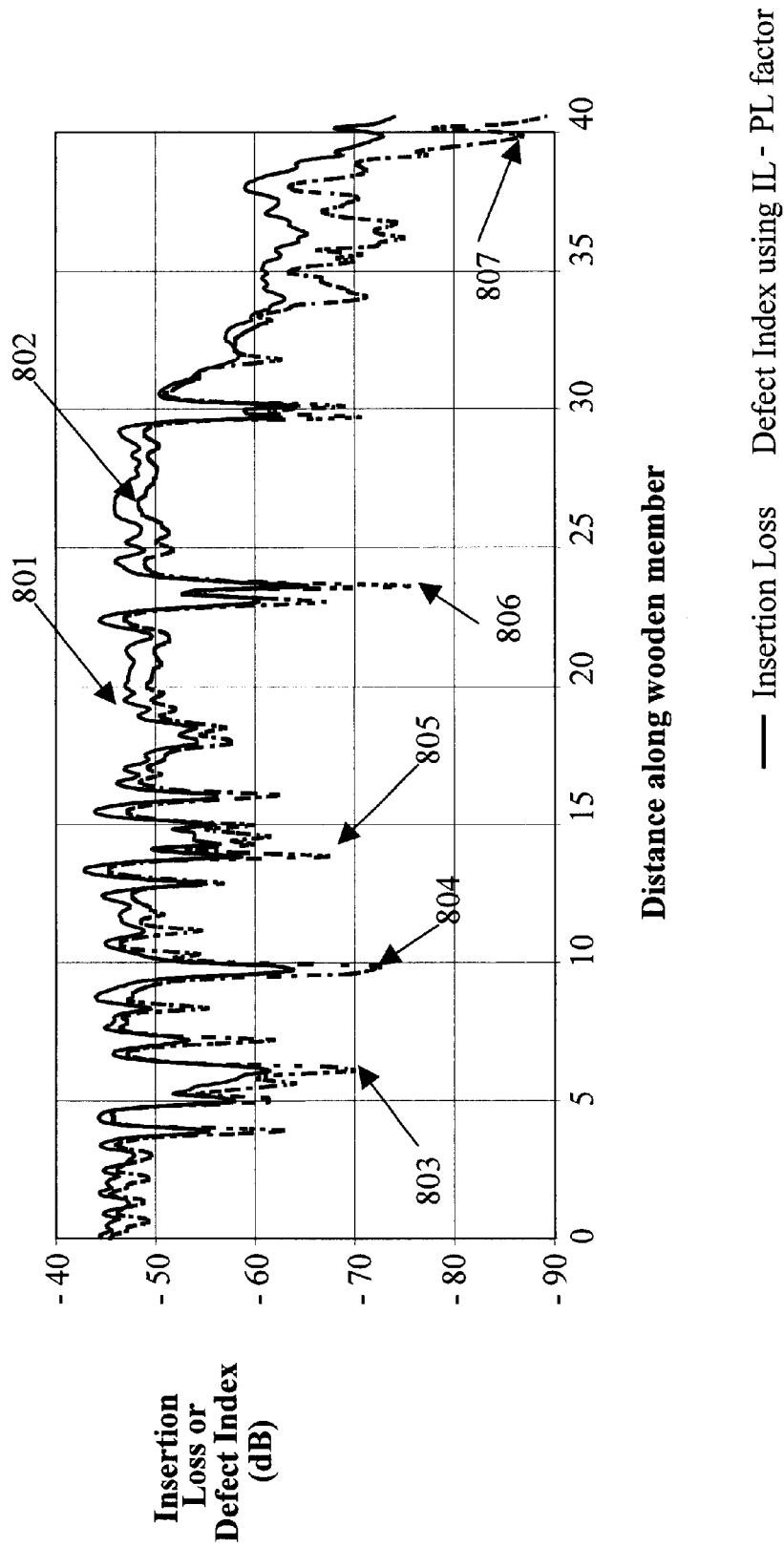
FIG. 8 is a graph of the insertion loss and defect index as a function of position along the same wooden member as shown in FIG. 7, according to the invention.

FIG. 7 provides a graph of the insertion loss waveform 701 and the pulse length waveform 702 as a function of position along a wooden member, taken across the grain of the wood. FIG. 8 is a corresponding plot of the insertion loss waveform 801 and a defect index waveform 802 as a function of position along the same wooden member as analyzed in FIG. 7. Comparison of FIGS. 7 and 8 further demonstrate the significance of using the defect index.

In FIG. 7, it is necessary to compare visually both insertion loss and pulse length to their respective reference values in order to determine the location, severity, or extent of a defect. Specifically, in defective regions of wooden member 100, the Insertion Loss decreases and the Pulse Length both increase. Thus, there is a coincidence of the two signals in the region of a defect. However, the defect index shown in FIG. 8 demonstrates how the regions of the various defects show more pronounced changes in the defect index graph than the corresponding regions of the insertion loss. In particular, reductions 803–807 in defect index waveform 802 reflect more pronounced reductions than the corresponding reductions in insertion loss waveform 801 that shadow reductions 803–807. Therefore, logarithmically combining the insertion loss and pulse length, instead of using either one independently, results a single parameter with a 15 dB to 20 dB improvement in defect detectability. This 15 dB to 20 dB improvement is especially significant in preventing ambient conditions or equipment inefficiencies (e.g., "noise") from adversely affecting the defect detection.

Table 1 below illustrates the advantages of using the defect index numerically. The "Good Waveform" is waveform 500 depicted in FIG. 5 that passed through normal, non-defective wood, and the "Distorted Waveform" is waveform 600 depicted in FIG. 6 that passed through a defective area of wood.

TABLE 1

|  | Insertion Loss (dB) | Pulse Length ($\mu$s) | Defect Index (dB) |
| --- | --- | --- | --- |
| Good Waveform (FIG. 5) | −56.39 | 120 | −63.43 |
| Distorted Waveform (FIG. 6) | −73.14 | 286 | −87.78 |
| Difference | 16.75 | 2.4X | 24.35 |

Using the defect index results in an increased difference in value between the "Good Waveform" and the "Distorted Waveform," as compared to using insertion loss and pulse length individually. In particular, the overall difference between the 16.75 dB change in insertion loss and the 24.35 dB change in defect index is an indication of the increased sensitivity to changes permitted by the defect index. In many defect measurement environments, the differences between "good" and "bad" signals can range up to 30 dB to 40 dB. The overall dynamic range between best signal and noise floor, where noise floor is the signal remaining when there is no contact with the wood, can be up to 60 dB. Therefore, the increased difference created by the defect index may overcome these ambient problems and provide good defect detection, while insertion loss and pulse length individually may not permit accurate defect detection.

Defect Index using Time of Flight, Pulse Length, and Insertion Loss

In another embodiment, a time of flight of a waveform may be used as a parameter in determining the defect index. Generally, time of flight is the time required for a sound wave to traverse an object. This may be calculated using a number of methods well known to those skilled in the art. These methods may include threshold detection, centroid estimation, or deconvolution, all of which have been disclosed in the following references: Beall, F. C., et al., "*Wood: Acoustic Emission and Acousto-Ultrasonic Characteristics*" Concise Encyclopedia of Materials Characteristics, R. W. Cahn and Eric Lifshin, Eds. Pergammon Press, pp. 551–554, (1993).; R. W. Cahn and Eric Lifshin, "*Concise Encyclopedia of Materials Characteristics*" eds. Pergammon Press, pp. 551–554, (1993); Beall, Frank C., "*Overview of Acousto-Ultrasonics Applied to Wood and Wood-Based Materials*", Topical Conference Proceedings Book, Second International Conference on Acousto-Ultrasonics, Atlanta, Georgia, Jun. 24–25, 1993, pp. 153–161; U.S. Pat. No. 5,760,308, to Beall et al., entitled "*Method and Apparatus for Non-Destructively Detecting Hidden Defects Caused by Bio-Deterioration in Living Trees and Round Wood Materials*"; and U.S. Pat. No. 5,804,728, to Beall et al., entitled "*Method and Apparatus for Non-Intrusively Detecting Hidden Defects Caused by Bio-Deterioration in Living Trees and Round Wood Materials*," incorporated herein by reference.

Figure 9:
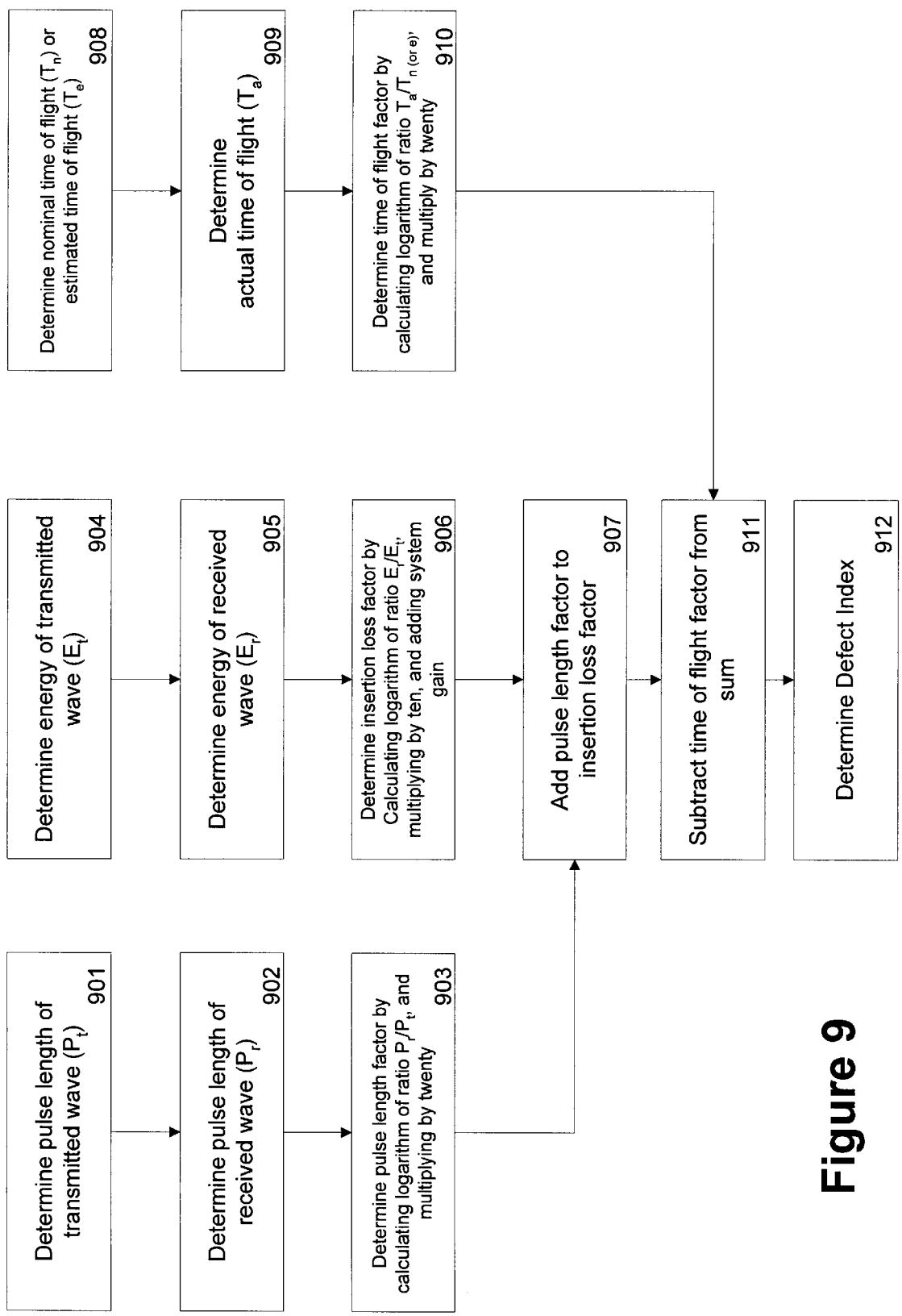
FIG. 9 is a flow diagram detailing another example for identifying defects in an object, according to the invention.

FIG. 9 is a flow diagram detailing another example for identifying defects in an object using time of flight, according to the invention. Steps 901–907 are identical to steps 401–407 in FIG. 4, and incorporate the pulse length factor and insertion loss factor into the defect index determination. In steps 908, a nominal time of flight ($T_n$) or an estimated time of flight ($T_e$) is determined. The estimated or nominal time of flight represents a base-line measurement upon which an actual time of flight ($T_a$) (determined in step 909) may be compared.

The estimated time of flight ($T_e$) may be determined using known values for the distance between transmitting transducer 202 and receiving transducer 203, for the expected speed of the wave in wooden member 100, and for the characteristics of the wave itself. In wooden members, for example, where the wave is ultrasonic, the expected speed of sound is a function of the direction of ultrasonic wave propagation with respect to the dominant wood fiber orientation, the species of the wood, and the moisture content of the wood. In most instances, these conditions can be estimated with reasonable certainty. The distance between the transducers and the expected speed of the wave may be inputted to computer 206. The characteristics of the wave may be determined by computer 206 via the connection to waveform generator 208. As a result, computer 206 may perform the desired calculations.

Alternatively, a nominal time of flight ($T_n$) may be determined in step 908. The nominal time of flight may be determined by measuring the time it takes a wave to travel from transmitting transducer 202 to receiving transducer 203, under ideal conditions. Such ideal conditions may include, for example, passing the wave through a material that is known to be free of defects. In this way, any subsequent changes in the time of flight (as compared to the nominal time of flight) can be considered to reflect the presence of anomalies in the material. The method selected for determining the baseline time of flight value from the various alternatives may depend upon the desired sophistication of anomaly detection.

In step 909, the actual time of flight ($T_a$) is determined. The actual time of flight represents the time it takes transmitted wave 204 to leave transmitting transducer 202, pass through wooden member 100, and be received as received wave 205 by receiving transducer 203. The time of flight value may be determined by computer 206. By comparing the actual time of flight to the estimated or nominal time of flight (as determined in step 908), the presence of anomalies may be detected.

In step 910, a time of flight factor is determined by calculating the logarithm of the ratio $T_r/T_n$ $_{(or\ e)}$ and multiplying by a factor of 20. In step 911, the time of flight factor is subtracted from the sum of the insertion loss factor and the pulse length factor that was determined in step 907. In step 912, a defect index is then determined. Therefore, in one embodiment where insertion loss, pulse length, and time of flight are used as the parameters, the defect index may be calculated, using the following equation:

$$DI(dB) = IL + 20\log\left[\frac{PL_r}{PL_t}\right] - 20\log\left[\frac{TOF_r}{TOF_n}\right]$$

This calculation may be performed by computer 206. In addition, the individual values needed to perform the calculation may be determined and stored within computer 206.

Figure 10:
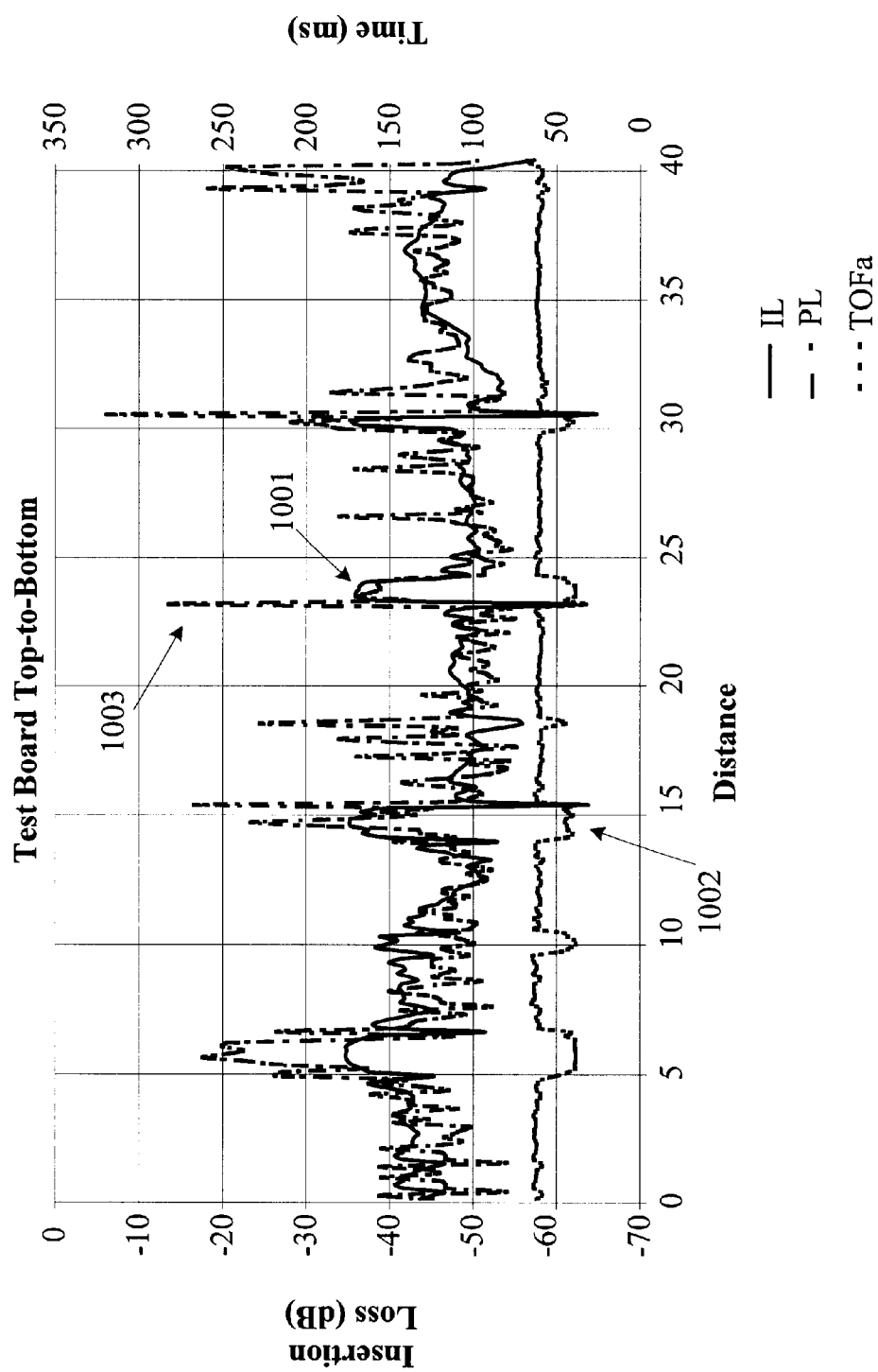
FIG. 10 is a graph of the insertion loss, pulse length, and time of flight.
Figure 11:
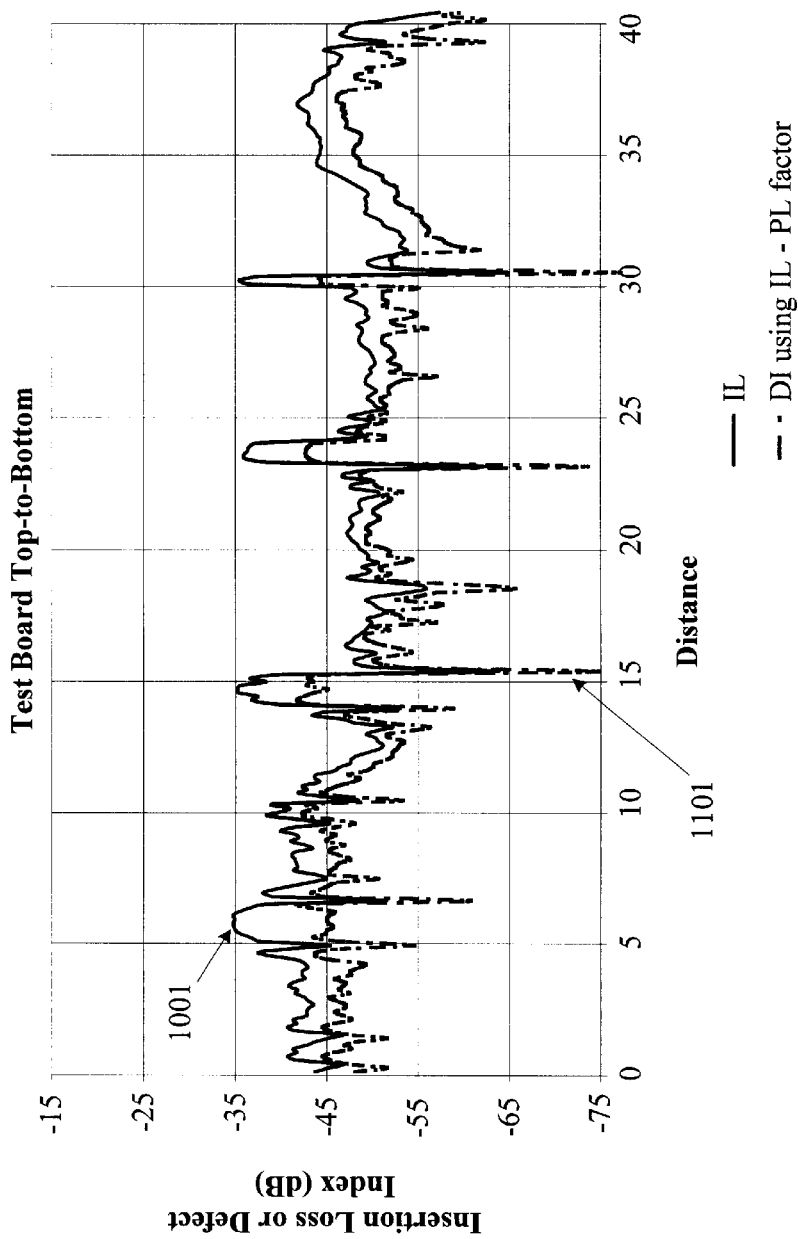
FIG. 11 is a graph of the insertion loss and defect index (using insertion loss, the pulse length factor, and the time of flight factor) as a function of position along the same wooden member as shown in FIG. 10, according to the invention.
Figure 12:
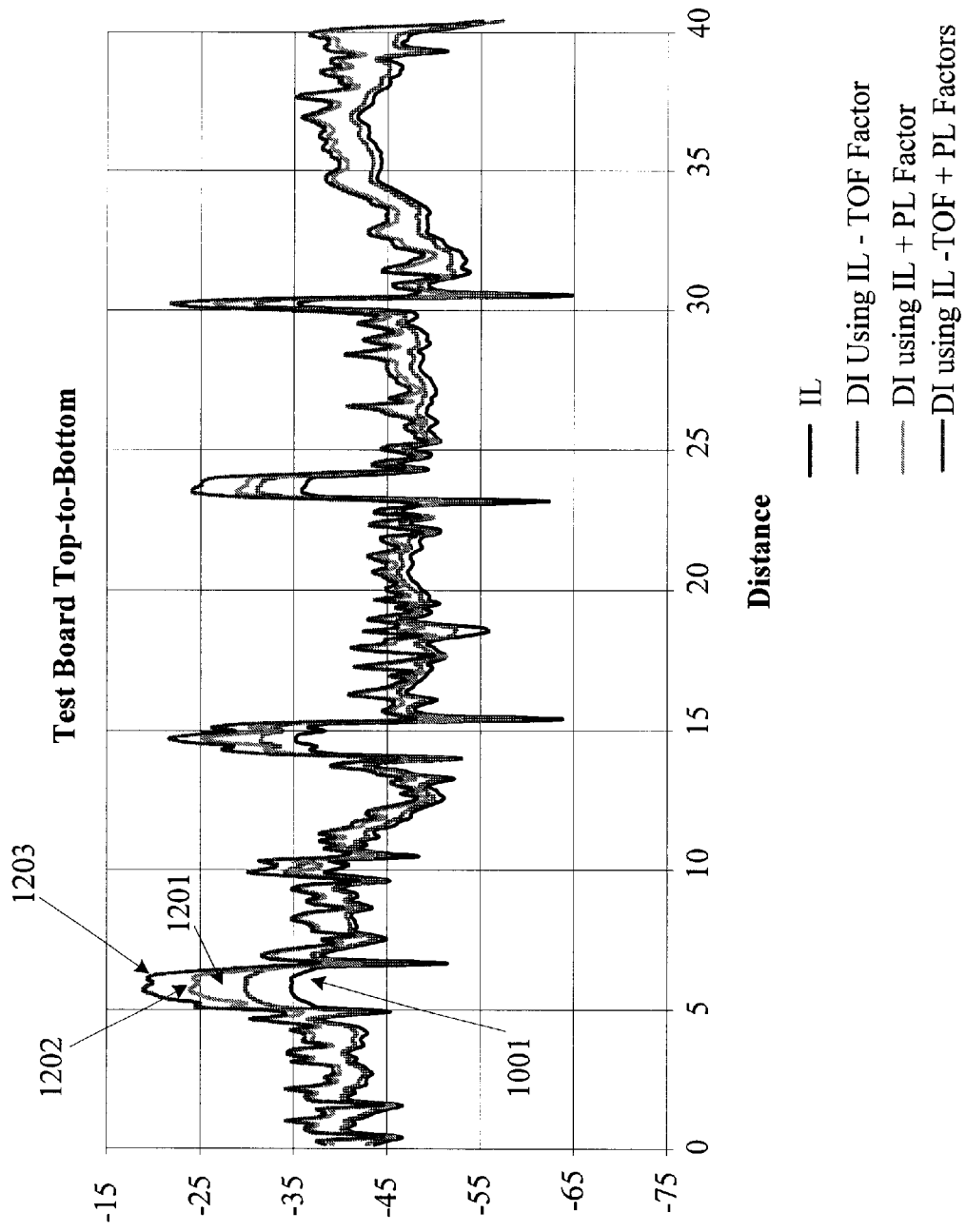
FIG. 12 is a graphical comparison of the insertion loss with three different defect indices as a function of position along the same wooden member as shown in FIG. 10, according to the invention.

FIGS. 10–12 graphically depict the advantage of using different defect index combinations. Note also that defects are shown in FIGS. 10–12 as an increase in signal level, consistent with an expected understanding of such a relation. FIG. 10 provides a graph of an insertion loss waveform 1001, a pulse length waveform 1002, and time of flight waveform 1003, individually as a function of position along a wooden member. Notably, in FIG. 10 the time of flight is denoted "TOFa" because it is based on an amplitude threshold algorithm as a function of position wooden member 100. FIG. 11 is a graph for the same wooden member as in FIG. 10 showing insertion loss waveform 1001 and one defect index waveform 1101, wherein waveform 1101 is determined by subtracting the pulse length factor from the insertion loss factor. FIG. 12 is a graph for the same wooden member as in FIG. 10 showing insertion loss waveform 1001 and three different defect index waveforms, as follows: (1) insertion loss factor minus time of flight factor waveform 1201; (2) insertion loss factor plus pulse length factor waveform 1202; (3) insertion loss factor minus time of flight factor, plus pulse length factor (as described with reference to FIG. 9) waveform 1203.

As shown in FIG. 12, there is a 10 dB improvement in the signal level in the region of the knot defects in the wooden member, when comparing the insertion loss waveform 1001 with the defect index waveform 1203 (i.e., the insertion loss less the time of flight factor, plus the pulse length factor). Therefore, FIG. 12 shows that by combining the insertion loss with the pulse length and the time of flight in a logarithmic fashion, there results a single parameter with a significant improvement in defect detectability.

It should be appreciated that the invention is not limited to the described combinations of the measurement parameters. On the contrary, those skilled in the art will understand that other combinations of measurement parameters in a logarithmic fashion using a reference level are possible. Which of the available combinations provide the most precise result will vary with the geometry of the object, the type of defects to be detected, and the orientation of the ultrasonic wave. It should also be appreciated that in some circumstances, it may be possible to use different combinations of the same parameters to form different defect indices, wherein each index is "tuned" to a specific defect.

For example, it is well known in the art that a knot defect in a wooden member have a specific effect upon ultrasound wave transmission. As such, a specific combination including both pulse length and time of flight may be most appropriate. On the other hand, a split or check defect in a wooden member, which is often induced through improper drying procedures, does not affect the time of flight, and has a different effect on insertion loss and pulse length. Accordingly, a split or check defect may be detected using a different combination than that which is applied to a knot defect. Thus both types of defects may be not only detected, but also differentially diagnosed from the same underlying measurement parameters, using the invention.

Defect Mapping Applications using Defect Index

There may be a plurality of applications for using the improved defect index parameter to display the existence of the defects. For example, it may be possible to further process the information and generate graphical or numerical "maps" of defective regions. Although the following discussion identifies two such methods for using the defect index to map anomalies, it should be appreciated that application of the invention is not limited to these two methods. The first method has proven very effective in locating large defects in wooden members, such as internal splits, check, honeycomb, rot, and pitch pockets. The second method is very sensitive to localized defects.

Figure 13:
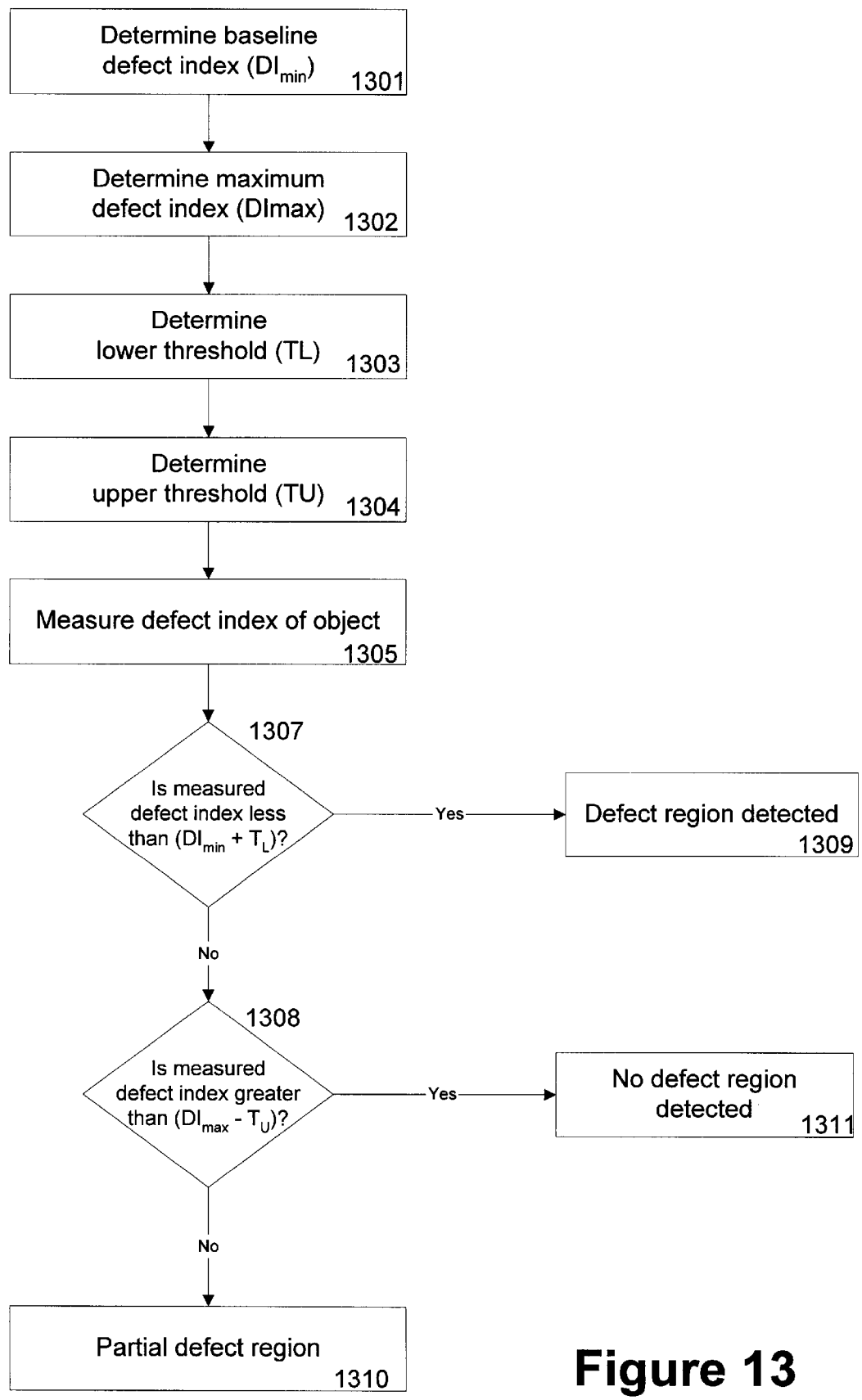
FIG. 13 is a flow diagram of one method of using the defect index to locate regions of defective material, especially suitable for extended regions of defects, such as splits or checks in wooden members, according to the invention.

FIG. 13 is a flowchart of a first method of using the defect index to locate regions of defective material. Generally, this method uses the defect index to identify general regions of internal defects that extend over a significant length of the object. For example, a split in a wooden member may extend from several inches to over one foot along the length of the member. In this case, as will be described, after the defect index is determined, a range of defect levels may be determined to decide which objects are defective and which are sound.

As shown in FIG. 13, in step 1301, a minimum defect index level ($DI_{min}$) is established. The minimum defect index level is determined by transmitting a wave from transmitting transducer 202 to receiving transducer 203 without any object present and no contact between the two transducers, such that essentially none of the transmitted wave reaches the receiver. By removing the object, the minimum defect index level measures system noise and other ambient interferences to establish a baseline value for the defect index. Therefore, the minimum defect index represents transmission through a maximally defective object (i.e., no appreciable transmission), and thus may represent the "worst" defect index attainable. In step 1302, a maximum defect index level ($DI_{max}$) is established. The maximum defect index may be determined statistically for a sample of objects with similar characteristics based on common and expected characteristics (e.g., species, moisture content, and size). The maximum defect index may be normalized using the distance between transmitting transducer 202 and receiving transducer 203 (e.g., the width of the object), and the size of the wave path between transmitting transducer 202 and receiving transducer 203 (i.e., the height of the object), as is well known to those skilled in the art. The maximum defect index also may be determined on an object-by-object basis, when a great deal of variability within the collection of objects is expected. However, in most manufacturing environments (e.g., a sawmill for wooden members) there is a high level of similarity among the variables listed above, especially on a "batch" basis.

Once the minimum and maximum defect indices have been determined, the user may establish two threshold intervals, a lower threshold ($T_L$) and an upper threshold ($T_U$). In step 1303, the lower threshold is established by selecting some value above the minimum defect index that will be considered a defective object. In step 1304, the upper threshold is established by selecting some value below the maximum defect index that will be considered to be an acceptable or sound object. In step 1305, the defect index of the material is measured (as described with reference to FIGS. 3, 4 and 9). In step 1306, if the measured defect index for a given position in the object is less than the lower threshold plus the minimum defect index, the object is labeled "bad" or "defective", at step 1309. In step 1307, if the measured defect index for a given position in the object is greater than the maximum defect index minus the upper threshold, the object is labeled "good" or "acceptable," at step 1311. In step 1308, any defect index that falls between these two levels is considered "suspect" or a "partially defective," at step 1310. This analysis may be performed by computer 206, where the precise values of $T_L$ and $T_U$ may be determined by an operator based on: (1) a general consistency of the object (e.g., wood versus steel); (2) the desired sensitivity to defect detection (i.e., is it more important not to reject some "good" material because of false readings, or more important to detect all s possible "bad" material); and (3) the electronic/mechanical noise environment.

Figure 14:
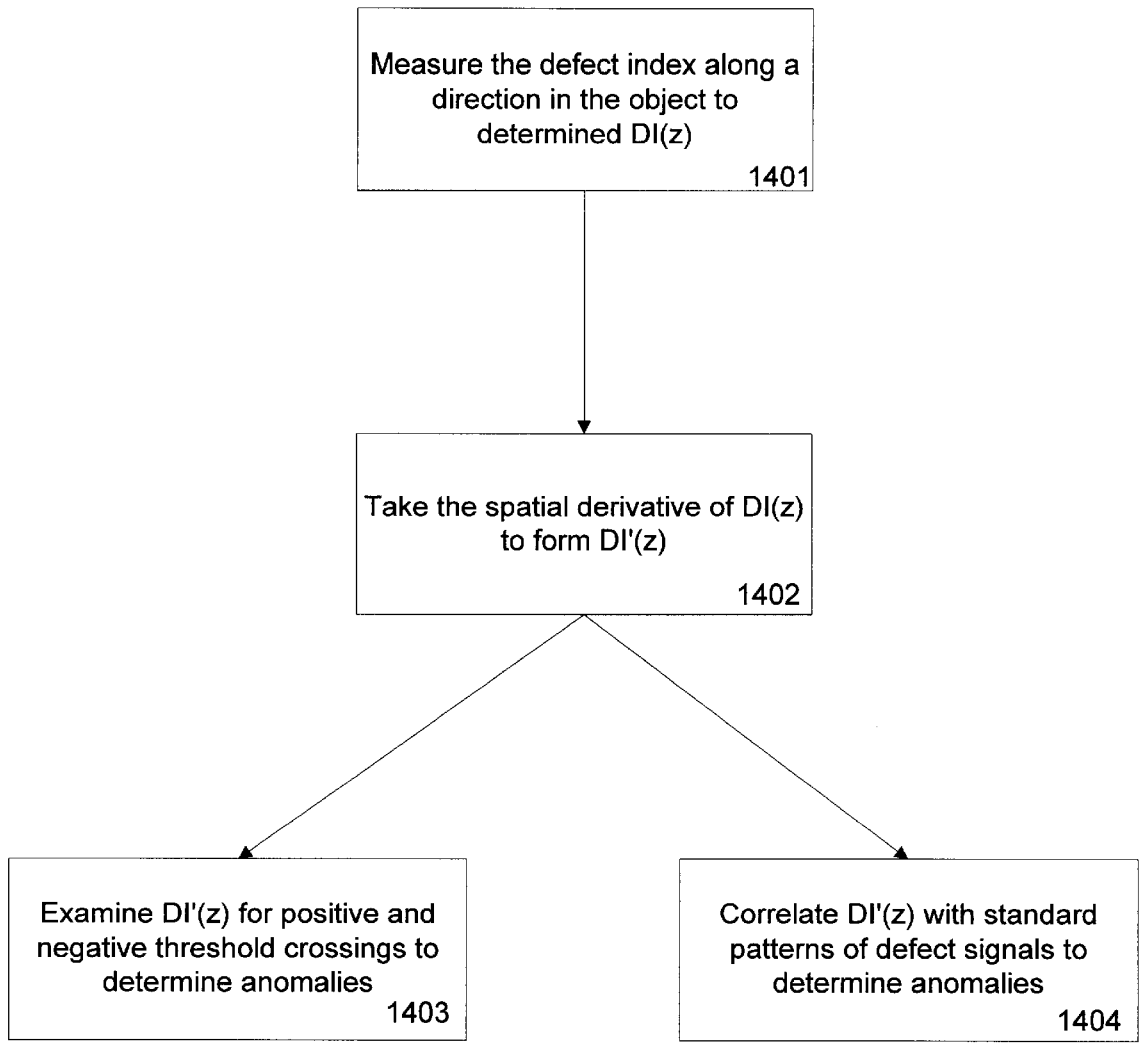
FIG. 14 is a flow diagram of another method of using the defect index to locate regions of defective material, especially suitable for locating small defects such as knots in wooden members, according to the invention.

One feature of the invention is that the measured defect index is uniquely sensitive to certain anomalies because it combines both energy and temporal parameters. For example, for knot defects in wooden members, the typical grain distortions that occur cause the defect index to display a pronounced drop in the region around a knot. This is so regardless of the average signal level of the surrounding wood. Therefore, using another mapping method, it is possible to find such localized defects. FIG. 14 is a flowchart of such a method.

The defect mapping method shown in FIG. 14 is especially suited for locating small defects such as knots in wooden members. In step 1401, the defect index is measured along one direction in the wooden member to form DI(z), for example longitudinal axis 104 (as shown in FIG. 1). For simplicity, the method shown in FIG. 14 scans a single line along the long axis of a wooden member, however, this may be accomplished along multiple axes. Moreover, it will be clear to those skilled in the art that the following approach may be generalized to more than one spatial dimension, and act upon data, for example, taken as DI(x,z). In step 1402, the positional derivative with respect to the scanning direction is determined. This positional derivative will be denoted dDI/dz, or DI'(z). The DI' (z) curve will show deviations which correspond to regions of rapid change in DI(z). These areas of rapid change typically correspond to knots or other small defects. Thus, by analyzing the DI' (z) curve, it is possible to find the defect regions regardless of the overall properties of the wood.

In order to conduct this analysis, one of two approaches is possible. The first, in step 1403, is simply to examine the DI' (z) curve for deviations above or below threshold levels. The operator may determine the exact values of thresholds, and must account for material type, typical size of knots, and consistency of the data, for example. An alternate approach, in step 1404, is to perform a pattern matching algorithm, such as decorrelation, with a fixed pattern that is typical of knots of the type found in the subject material. Such decorrelation is well-known to those skilled in the art.

In sum, the invention allows for the simultaneous inclusion of a plurality of parameters, including energy, time, and distance parameters into a single numerical defect index. Because the invention allows a flexible combination of these various parameters, it is uniquely suited to identify defects in wood and other similar non-homogeneous materials. In addition, the defect index of the invention is especially sensitive to small changes. The defect index's sensitivity is especially useful for some objects, like wood, where the natural characteristics tend to both reduce the amplitude, and extend the temporal duration of the received signal. As a result, the invention provides immediate improvement in the dynamic range of the defect detection system, relative to strongest detected signal to the noise floor. The lack of a signal, such as the ultrasound transducers not being in contact with the wood, not only reduces the energy (the first part of the defect index), it also increases the apparent pulse duration (the second part of the defect index). This increased dynamic range and signal to noise ratio has increased the invention's defect detectability.

The invention is directed to a system and method for detecting anomalies in an object. Although the invention was described in the context of wooden members and ultrasonic waveforms, it is not so limited. In fact, the invention may be applied to other objects using acoustic waves in other frequency ranges, for example, seismic waves, sonar waves, and/or electromagnetic waves. It will be understood that the present invention is not limited to use of any of the particular components or devices herein. Indeed, this invention can be used in any application that detects anomalies in objects. Further, the system disclosed in the present invention can be used with the method of the present invention or a variety of other applications.

While the invention has been particularly shown and described with reference to the presently preferred embodiments thereof, it will be understood by those skilled in the art that the invention is not limited to the embodiments specifically disclosed herein. Those skilled in the art will appreciate that various changes and adaptations of the invention may be made in the form and details of these embodiments without departing from the true spirit and scope of the invention as defined by the following claims.

What is claimed is:

1. A method of identifying anomalies in an object, comprising the steps of:

(a) transmitting a wave through said object;

(b) receiving said wave after passage through said object;

(c) measuring more than one characteristic of said received wave;

(d) determining more than one reference characteristic;

(e) comparing a first reference characteristic with a first characteristic of said received wave to create a first factor;

(f) comparing a second reference characteristic with a second characteristic of said received wave to create a second factor;

(g) combining said first factor with said a second factor to create a defect index; and (h) identifying one or more anomalies in said object using said defect index.

2. The method of claim 1, wherein said step of determining said reference characteristics comprises:

(a) transmitting another wave of known characteristics through a material free of anomalies to produce a standard wave; and (b) measuring one or more characteristics of said standard wave.

3. The method of claim 1, wherein said step of determining said reference characteristics comprises calculating said reference characteristics from known values of said transmitted wave.

4. The method of claim 1, further comprising the step of storing said reference characteristics in a computer.

5. The method of claim 1, wherein each of said steps of comparing comprise the step of calculating a ratio of said reference characteristic to said characteristic of said received wave.

6. The method of claim 5, further comprising the step of calculating a logarithm of each of said ratios before conducting said step of combining.

7. The method of claim 1, further comprising the step of creating a graphical map of said anomalies with reference to said object.

8. The method of claim 1, wherein said characteristics include one or more of the following: pulse length, time of flight, and energy.

9. The method of claim 1, further comprising the step of outputting said locations of said identified anomalies to a grading apparatus for grading said object.

10. The method of claim 1, further comprising the step of outputting said locations of said identified anomalies to a device that cuts said object.

11. The method of claim 1, further comprising the steps of:

moving said object such that another portion of said object may be interrogated by said waves; and repeating steps (a) through (h).

12. The method of claim 1, wherein said step of transmitting said waves comprises transmitting ultrasonic waves.

13. The method of claim 1, wherein said step of transmitting said waves comprises transmitting at least one of the following: electromagnetic waves, seismic waves, and acoustic waves.

14. A system for detecting anomalies in an object, comprising:

a waveform generator that creates waves having one or more characteristics;

a transmitting transducer in communication with said waveform generator that transmits said waves through said object;

a receiving transducer that receives said waves after passage through said object; and a computer in communication with said receiving transducer and said transmitting transducer that:

stores reference characteristics;

compares a first reference characteristic with a first characteristic of said received wave to create a first factor;

compares a second reference characteristic with a second characteristic of said received wave to create a second factor;

combines said first factor with said second factor to create a defect index; and identifies a location of one or more anomalies in said object using said defect index.

15. The system of claim 14, further comprising a display device in communication with said computer, wherein said display device displays a graphical map of one or more anomalies within said object.

16. The system of claim 14, further comprising a conveyor device that moves said object between said transmitter and said receiver.

17. The system of claim 16, further comprising a positional encoder in communication with said conveyor device and said computer, wherein said positional encoder provides said computer with a position of said object with respect to said transmitting transducer and said receiving transducer.

18. The system of claim 14, wherein one of said characteristics is time of flight.

19. The system of claim 14, wherein one of said characteristics is energy.

20. The system of claim 14, wherein one of said characteristics is a pulse length.

21. The system of claim 20, wherein said pulse length is 1.25 multiplied by a time it takes said wave to rise from ten percent to ninety percent of its final energy value.

22. The system of claim 14, wherein said object comprises wood.

23. The system of claim 14, wherein said waves are ultrasonic waves.

24. The system of claim 14, wherein said waves are at least one of the following:

electromagnetic waves, seismic waves, and acoustic waves.

25. A method of identifying anomalies in an object, comprising the steps of:

(a) transmitting a wave through said object;

(b) receiving said wave after passage through said object;

(c) measuring a first and a second characteristic of said received wave;

(d) determining a first and a second reference characteristic;

(e) calculating a first ratio of said first reference characteristic to said first characteristic of said received wave;

(f) calculating a second ratio of said second reference characteristic to said second characteristic of said received wave;

(g) calculating a logarithm of said first ratio to create a first factor;

(h) calculating a logarithm of said second ratio to create a second factor;

(i) combining said first factor with said second factor to create a defect index;

(j) identifying one or more anomalies in said object using said defect index;

(k) storing said reference characteristics of said wave in a computer;

(l) moving said object such that another portion of said object may be interrogated by said waves; and (m) repeating steps (a) through (l).

26. The method of claim 25, wherein said step of determining said reference characteristics comprises:

(e) transmitting a wave of known characteristics through a material free of anomalies to produce a standard wave; and (f) measuring one or more characteristic of said standard wave.

27. The method of claim 25, wherein said step of determining said reference characteristics comprises calculating said characteristics from known values of said transmitted wave.

28. The method of claim 25, further comprising the step of creating a graphical map of said anomalies with reference to said object.

29. The method of claim 25, further comprising the step of outputting said locations of said identified anomalies to a grading apparatus for grading said object.

30. The method of claim 25, further comprising the step of outputting said locations of said identified anomalies to a device that cuts said object.

* * * * *